(12) United States Patent
Dolgos et al.

(10) Patent No.: US 7,873,489 B2
(45) Date of Patent: Jan. 18, 2011

(54) DIALYSIS MACHINE WITH SERVICING INDICATOR

(75) Inventors: Sándor Dolgos, Szentendre (HU); G. Róbert Schin, Budapest (HU); Stefan Moll, Melsungen (DE)

(73) Assignee: B. Braun Medizintechnologie GmbH, Melsungen (DE)

( * ) Notice: Subject to any disclaimer, the term of this patent is extended or adjusted under 35 U.S.C. 154(b) by 224 days.

(21) Appl. No.: 11/365,538

(22) Filed: Mar. 1, 2006

(65) Prior Publication Data

US 2006/0265180 A1    Nov. 23, 2006

(30) Foreign Application Priority Data

Mar. 4, 2005    (EP)    ................................. 05101697

(51) Int. Cl.
*G06F 15/00*    (2006.01)
(52) U.S. Cl. .................. 702/117; 702/177; 702/34; 702/184; 210/85; 210/646; 210/143; 700/83
(58) Field of Classification Search ................ 702/117, 702/177, 34, 184; 210/85, 646, 143; 700/83; 600/513; 128/903–904; 705/2–4
See application file for complete search history.

(56) References Cited

U.S. PATENT DOCUMENTS

| | | | | |
|---|---|---|---|---|
| 4,525,782 A | * | 6/1985 | Wohlfarth et al. ............. | 701/99 |
| 4,539,632 A | * | 9/1985 | Hansen et al. ................ | 700/14 |
| 5,629,871 A | * | 5/1997 | Love et al. .................... | 702/34 |
| 5,701,249 A | * | 12/1997 | Berson ........................ | 705/408 |
| 6,138,056 A | * | 10/2000 | Hardesty et al. ............ | 700/174 |
| 6,876,908 B2 | | 4/2005 | Cramer et al. | |
| 2004/0148083 A1 | * | 7/2004 | Arakawa et al. .............. | 701/50 |

FOREIGN PATENT DOCUMENTS

| | | |
|---|---|---|
| DE | 3828224 | 2/1990 |
| DE | 4131247 | 4/1993 |
| DE | 19832825 | 12/1999 |
| DE | 10015450 | 10/2001 |
| DE | 10148214 | 4/2003 |
| EP | 1331589 | 1/2003 |
| WO | WO96/40316 | 12/1996 |

OTHER PUBLICATIONS

Paulo Gil Siqueira de Faria (Monitorization of maintenance cost for hemodialysis machine, J Bras Nefrol 2005).*

* cited by examiner

*Primary Examiner*—Drew A Dunn
*Assistant Examiner*—Hien X Vo
(74) *Attorney, Agent, or Firm*—RatnerPrestia

(57) ABSTRACT

A dialysis machine that monitors an elapsed time and a number of accumulated hours during a current servicing interval is disclosed. The machine executes a machine-servicing algorithm on at least the elapsed time and the accumulated operating hours to generate a projected servicing interval duration. A servicing event indicator displays servicing event schedule information based on the projected servicing interval duration. A transfusion pump, similarly equipped, is also provided.

17 Claims, 1 Drawing Sheet

DIALYSIS MACHINE WITH SERVICING INDICATOR

This patent application claims priority of European patent application number 05101697.0, filed Mar. 4, 2005, the entire disclosure of which is incorporated herein by reference.

BACKGROUND OF THE INVENTION

The invention refers to a dialysis machine for extracorporeal blood treatment, namely for the removal of contaminants from blood, and in particular to a dialysis machine comprising a servicing event indicator.

Dialysis machines include a complex system for the purification of blood taken from a patient's body. The dialysis machine comprises a blood circuit and a dialysate circuit respectively passing through different chambers of a dialysis machine in which the contaminants are removed from the blood. The dialysis machine includes liquid conveying systems with numerous pumps for feeding the dialysate and the blood, as well as for preparing the dialysate from various liquids and for maintaining temperature. Further, a complex control and monitoring system with numerous sensors and operating components is provided. For example, the sensors include conductivity sensors, pressure gauges, temperature sensors and the like. The operating components mainly comprise pumps and valves.

Since failure of a dialysis machine could become fatal for a patient connected thereto, each machine must be maintained on a regular basis following specific regulations. Such preventive servicing event may be prescribed by authorities. Moreover, the individual manufacturers have their own servicing event regulations. Servicing event regulations generally provide servicing intervals in the form of specific fixed periods of time. Most common is a servicing event on an annual or biennial basis. For economic reasons, however, increasingly longer servicing intervals are demanded. Yet, too long a servicing interval may incur a risk of device failure during the treatment and thus may also cause high costs due to patients' complaints and unscheduled equipment downtime.

EP 1 331 589 A2 describes a medical apparatus that is adapted to detect the onset of problems and to transmit notification of such to servicing event personnel via a remote transmission system so as to inform the personnel of a needed repair. Here, the repair happens only after a trouble has been detected, which in the case of dialysis machines is oftentimes too late.

SUMMARY OF THE INVENTION

In one aspect, the invention provides a dialysis machine including means for monitoring an elapsed time and a number of accumulated operating hours for the machine during a current servicing interval. The machine also includes calculating means for executing a machine-servicing algorithm on at least the elapsed time and the accumulated operating hours to generate a projected servicing interval duration, and a servicing event indicator including means to display servicing event schedule information based on the projected servicing interval duration.

In another aspect, the invention provides a transfusion pump equipped in a manner analogous to that described immediately above for a dialysis machine.

In further aspects, the invention provides a method of servicing a dialysis machine or a transfusion pump as described above. The method includes servicing one or more components, or resetting the means for monitoring-elapsed time or number of actual operating hours, on the dialysis machine or transfusion pump.

DETAILED DESCRIPTION OF THE INVENTION

Figure 1:
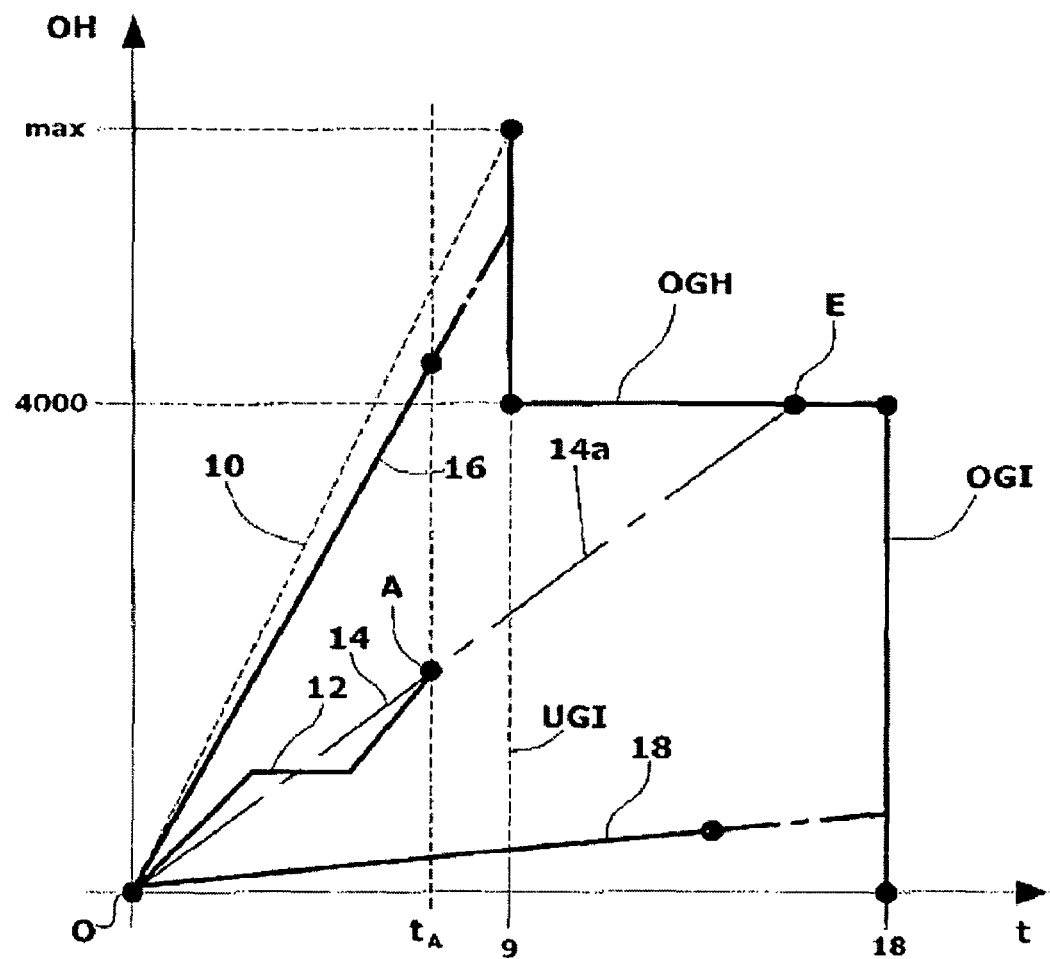
FIG. 1 shows a diagram illustrating an exemplary protocol for determining a servicing interval for a dialysis machine, according to the invention.

The invention provides a dialysis machine having a servicing event indicator that notifies the user of an upcoming recommended servicing event, for example by means of a display device (typically a visual display such as a liquid crystal or light emitting diode display) on or connected to the machine. The displayed recommended timing is arrived at by a calculation based upon the usage history of the machine. Typically, the calculation will include at least one or both of 1) the elapsed time and 2) the number of accumulated operating hours since the last servicing event. Other usage history parameters may also be included. Typically, the collection of usage history information and the calculation of the recommended servicing will be performed by a microprocessor, either integral with or connected to the machine, operating according to a predetermined algorithm to determine the recommended duration for the current servicing interval (i.e., the period since the most recent servicing).

A dialysis machine so equipped will determine the proper time for the next scheduled servicing event and inform the dialysis machine operator in time to schedule servicing. It is contemplated that the resulting servicing event schedule may prevent a heavily used apparatus from being serviced too seldom and thereby presenting a safety hazard, and, on the other hand, and also prevent an infrequently used apparatus from being serviced too often, thus incurring unnecessary effort and cost. It should be noted that, although the majority of the discussion herein relates to methods and apparatus involving dialysis machines, the same approaches may also be used for transfusion pumps, which share with dialysis machines a high reliability and safety requirement.

Besides the two factors mentioned, the calculation of the servicing interval may also incorporate other factors such as the age of the dialysis machine, the total number of operating hours worked, as well as the number of operating hours of particularly critical components.

In some embodiments of the invention, a servicing interval ends when an upper limit of the number of operating hours is reached, but not before a lower limit of the duration of the current servicing interval is reached. This means that in any case the servicing interval has a certain minimum duration. Only when the minimum duration is exceeded does the number of operating hours give the upper limit of the servicing interval. Other algorithms may also be formed from the two parameters mentioned, and optionally others.

The current time-in-service (i.e., the elapsed calendar time since the machine was put in service) of the dialysis machine can be included as a parameter in the algorithm for determining the duration of the current servicing interval, for example by decreasing the upper limit of the number of operating hours and/or by decreasing the lower limit of the duration of the current servicing interval as the time-in-service increases. Alternatively, or in addition, the total number of the accumulated operating hours to date may be included as a parameter.

Dialysis machines can operate on different programs or in different modes, and not all machine components may be used in all modes. Further, a dialysis machine includes certain components, such as certain pumps and/or valves, that may be of particular importance in terms of safety. Accordingly, in this invention these or other components may be monitored individually, with each selected component having its own history determined and stored. Thus, in some embodiments of the invention, the number of operating hours of a given machine component may be counted independently of the rest of the dialysis machine's operation. For example, upon determining the servicing interval for a given component, only those modes in which the machine component is actually used may be considered. Thus, the servicing event indicator might read: "replace valve seal", for example, and the criterion for this servicing event indicator might be derived from the duration of the current servicing interval of this valve and the number of operating hours of this valve.

Further, the servicing interval of the components may be based on the number of wear-causing cycles encountered by a given component. With valves, for example, these are switching cycles, i.e., an opening and a subsequent closing of the valve. The number of cycles that have occurred may be determined in any of a number of ways. For example, the number of actuation signals sent to the valve may be counted, or separate indications such as pressure surges caused by the opening of the valve may be counted. The speed or frequency at which the valve switches may also be of relevance to the rate of wear. The number of switching cycles per unit time may vary, depending upon the kind of therapy and the type of valve. With motors, a wear-causing cycles is defined by one rotation of the motor, and this can be counted through the control signal or by direct measurement at the motor. Another important factor of wear is the number of thermal and chemical loads during the disinfection of the components. With sealing elements, for example, each disinfection performed can be called a cycle causing wear and be counted as such. The number of cycles causing wear per time may of course vary widely for the various components, depending inter alia upon the type of component and the modes of operation in which the component is used.

The number of wear-causing cycles or actual operating hours in the current servicing interval may be determined and stored separately for one or more of the components, and in some embodiments it may be desired to monitor and indicate the servicing event criteria separately for a plurality of critical machine components. Here, a service monitoring device can also be configured such that, in the event of a servicing event point in time for a certain machine component, it calculates in advance whether the servicing intervals of other machine components will also lapse within so short a time that all upcoming servicing event operations might be bundled together.

Using the information and parameters described hereinabove, operated on by a suitable calculation means employing a predetermined algorithm, an indication of the desired timing of the next servicing event may be provided.

Turning now to FIG. 1, there is shown a diagram for determining the duration of a servicing interval for a dialysis machine according to one embodiment of the invention. In the diagram, the time t elapsed during the current servicing interval (beginning at point "O", the time of last servicing event) is plotted in months along the abscissa, and the number of actual operating hours OH (Operating Hours) accumulated during the current servicing interval is plotted along the ordinate. The dialysis machine includes a means for monitoring both of these parameters, and upon servicing event, the service technician resets both of these to 0, thereby starting a new servicing interval.

The duration of the servicing interval is not fixedly predetermined, but is determined according to the criteria to be explained in detail.

The dashed line 10 represents the maximum possible number of operating hours that would be obtained if the machine were operating every day for 24 hours over nine months. The lower time limit UGI of the current servicing interval is of a predetermined value, for example nine months in the present example. This means that the duration of the servicing interval is at least nine months, regardless of the number of operating hours. The upper limit OGH for the number of operating hours is also predetermined, for example 4,000 operating hours in FIG. 1. Further, a predetermined upper time limit OGI is provided for the duration of the current servicing interval, 18 months in this example. Thus in this example, the servicing interval will still end after 18 months, even if the machine is not used at all.

Curve 12 represents an exemplary plot of accumulated operating hours during the current servicing interval, as a function of elapsed time during the interval. At any given current time $t_A$, the calculating means calculates the average slope of the curve 12 between the points O and A and determines a straight line 14 whose extension 14a reaches the operating hours limit OGH at the point E. It results therefrom that upon a continuation of the operation at the average intensity of the curve 12, the expected end of the servicing interval will be at the point E, i.e., at approximately 16 months in this example.

Curve 16 refers to a case of frequent use. In this case, the operating hours limit of 4,000 hours would be exceeded before 9 months have passed, and thus the servicing interval would end at the lower time limit UGI of 9 months.

Curve 18 illustrates a case of infrequent use of the dialysis machine. Here, the servicing interval would end at the upper time limit OGI (18 months in the example shown). The limits UGI, OGH, OGI mentioned may be set differently depending on the local market requirements. More stringent reliability requirements may necessitate tighter limits, for example in certain markets or for certain customers. Similar algorithms may be executed for a given component of the machine, for instance a valve or a pump, etc.

Servicing event schedule information may be calculated and displayed on the dialysis machine, using the current values of 1) actual operating hours and 2) actual elapsed time (AE) during the current servicing interval. These may be constantly monitored, and accordingly an extrapolated projection of the total duration (OE) of the servicing interval may be constantly calculated, to thereby arrive at a servicing event schedule. That is, the timing of the next servicing event may be projected. One exemplary way in which this may be done is as follows.

The remaining percentage X of the total projected duration of the servicing interval may be calculated according to the equation $$X=(OE-AE)/OE*100.$$

The value of X may be constantly calculated in the dialysis machine and displayed, and will progress toward zero as the end of the servicing interval approaches. Thus, the operator will be apprised in advance of the impending need for servicing event, and can arrange for servicing event to occur at the appropriate time. In some embodiments, the servicing event schedule information may take the form of a projected servicing event date, or it may be displayed as the projected remaining amount of time before the end of the servicing interval.

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A dialysis machine comprising:
    means for monitoring the time elapsed since a prior servicing event and a number of operating hours accumulated by the machine since the prior servicing event;
    calculating means for executing a machine-servicing algorithm to generate a projected servicing interval duration, the projected servicing interval duration generated using the time elapsed and the number of operating hours accumulated since the prior servicing event; and
    a servicing event indicator comprising means to display servicing event schedule information based on the projected servicing interval duration.

2. The dialysis machine of claim 1, wherein the projected servicing interval duration is equal to an extrapolated time to reach a predetermined operating hours limit, provided however that the duration must not be less than a predetermined lower time limit and not more than a predetermined upper time limit.

3. The dialysis machine of claim 1, wherein the algorithm is adapted to additionally operate on the time-in-service of the dialysis machine.

4. The dialysis machine of claim 1, wherein the algorithm is adapted to additionally operate on the total number of operating hours accumulated during all servicing intervals to date.

5. The dialysis machine of claim 1, further comprising means for monitoring a number of accumulated operating hours or a number of actuation events for a component of the machine during a current servicing interval, wherein the calculating means comprises means for executing a component-servicing algorithm on at least the accumulated operating hours or the number of actuation events for the component, thereby generating a projected component servicing interval duration, and wherein the servicing event indicator further comprises means to display servicing event schedule information for the component based on the projected component servicing interval duration.

6. The dialysis machine of claim 5, wherein the calculating means further comprises means for executing the component-servicing algorithm on at least the accumulated operating hours for the component.

7. The dialysis machine of claim 5, wherein the calculating means further comprises means for executing the component-servicing algorithm on at least the number of actuation events for the component.

8. The dialysis machine of claim 5, wherein the means for monitoring the number of accumulated operating hours or the number of actuation events for the component comprises means for monitoring these parameters for each of a plurality of components, and wherein the calculating means comprises means for executing a component-servicing algorithm for each of the plurality of components, thereby generating a projected component servicing interval duration for each.

9. The dialysis machine of claim 1, wherein the display is a visual display.

10. The dialysis machine of claim 1, wherein the servicing event schedule information comprises the date corresponding to the end of the projected servicing interval.

11. The dialysis machine of claim 1, wherein the servicing event schedule information comprises the time remaining in the current scheduling interval in terms of hours, days, or weeks.

12. The dialysis machine of claim 1, wherein the servicing event schedule information comprises the time remaining in the current scheduling interval, indicated as a percent of the projected servicing interval duration.

13. A method of servicing a dialysis machine, the dialysis machine having means for monitoring the time elapsed since a prior servicing event and a number of operating hours accumulated by the machine since the prior servicing event, the dialysis machine also having calculating means for executing a machine-servicing algorithm to generate a projected servicing interval duration, the projected servicing interval duration generated using the time elapsed and the number of operating hours accumulated since the prior servicing event, and the dialysis machine also having a servicing event indicator including means to display servicing event schedule information based on the projected servicing interval duration, the method comprising:
    servicing one or more components or resetting the means for monitoring the time elapsed and the number of operating hours accumulated of the dialysis machine.

14. A transfusion pump comprising:
    means for monitoring the pump the time elapsed since a prior servicing event and a number of operating hours accumulated by the pump since the prior servicing event;
    calculating means for executing a pump-servicing algorithm to generate a projected servicing interval duration, the projected servicing interval duration generated using the time elapsed and the number of operating hours accumulated since the prior servicing event; and
    a servicing event indicator comprising means to display servicing event schedule information based on the projected servicing interval duration.

15. The transfusion pump of claim 14, wherein the projected servicing interval duration is equal to an extrapolated time to reach a predetermined operating hours limit, provided however that the duration must not be less than a predetermined lower time limit and not more than a predetermined upper time limit.

16. A method of servicing a transfusion pump, the transfusion pump having means for monitoring the time elapsed since a prior servicing event and a number of operating hours accumulated by the pump since the prior servicing event, the transfusion pump also having calculating means for executing a pump-servicing algorithm to generate a projected servicing interval duration, the projected servicing interval duration generated using the time elapsed and the number of operating hours accumulated since the prior servicing event, and the transfusion pump also having a servicing event indicator including means to display servicing event schedule information based on the projected servicing interval duration, the method comprising:
    servicing one or more components or resetting the means for monitoring the time elapsed the number of operating hours accumulated of the pump.

17. The dialysis machine of claim 1, further comprising means for monitoring an age of the machine, wherein the projected servicing interval duration is also generated using the age of the machine.

* * * * *